(12) United States Patent
Mulakkapurath Narayanan et al.

(10) Patent No.: US 10,227,633 B2
(45) Date of Patent: Mar. 12, 2019

(54) PORTABLE DEVICE FOR PURIFYING BIOLOGICAL SAMPLE AND A METHOD THEREOF

(71) Applicant: BIGTEC PRIVATE LIMITED, Rajajinagar, Bangalore, Karnataka (IN)

(72) Inventors: Manoj Mulakkapurath Narayanan, Bangalore (IN); Chandrasekhar Bhaskaran Nair, Bangalore (IN)

(73) Assignee: BIGTEC PRIVATE LIMITED, Bangalore (IN)

( * ) Notice: Subject to any disclaimer, the term of this patent is extended or adjusted under 35 U.S.C. 154(b) by 0 days.

(21) Appl. No.: 15/288,781

(22) Filed: Oct. 7, 2016

(65) Prior Publication Data
US 2018/0100182 A1    Apr. 12, 2018

(51) Int. Cl.
| | | |
|---|---|---|
| C12Q 1/686 | (2018.01) | |
| C12Q 1/6806 | (2018.01) | |
| B01L 7/00 | (2006.01) | |
| B01L 3/00 | (2006.01) | |

(52) U.S. Cl.
CPC .............. *C12Q 1/6806* (2013.01); *B01L 7/52* (2013.01); *B01L 3/527* (2013.01); *B01L 2200/04* (2013.01); *B01L 2300/024* (2013.01); *B01L 2300/027* (2013.01); *B01L 2300/0663* (2013.01); *B01L 2400/0478* (2013.01); *B01L 2400/0487* (2013.01); *B01L 2400/0622* (2013.01); *B01L 2400/0644* (2013.01)

(58) Field of Classification Search
CPC .. C12N 15/1006; G01N 1/405; C12Q 1/6806; B01L 3/502; B01L 2400/06; B01L 2200/0631; B01L 2300/087
See application file for complete search history.

(56) References Cited

U.S. PATENT DOCUMENTS

| | | | |
|---|---|---|---|
| 2004/0086870 A1* | 5/2004 | Tyvoll ............... | B01L 3/502715 435/6.19 |
| 2007/0292941 A1* | 12/2007 | Handique ............. | B01L 3/5027 435/288.7 |
| 2011/0100101 A1* | 5/2011 | Zenhausern ......... | G01N 21/645 73/64.56 |

* cited by examiner

*Primary Examiner* — Sally A Merkling
(74) *Attorney, Agent, or Firm* — Keller Jolley Preece

(57) ABSTRACT

The present disclosure provides a portable device for purifying biological sample. The device comprises a housing and a cartridge holder accommodated in the housing for holding at least one cartridge configured to purify the biological sample. At least one pump is positioned in the housing which is fluidly connectable to the cartridge to circulate the sample and one or more fluids through the cartridge. Further, at least one heating element is configured to heat a matrix chamber in the cartridge. At least one actuator is disposed in the housing to actuate one or more valves to selectively route the biological sample and the one or more fluids in the cartridge. A control unit is interfaced with the actuator, the heating element and the pump and is configured to regulate operation of the actuator, the pump and the heating element during purification of the biological sample.

13 Claims, 9 Drawing Sheets

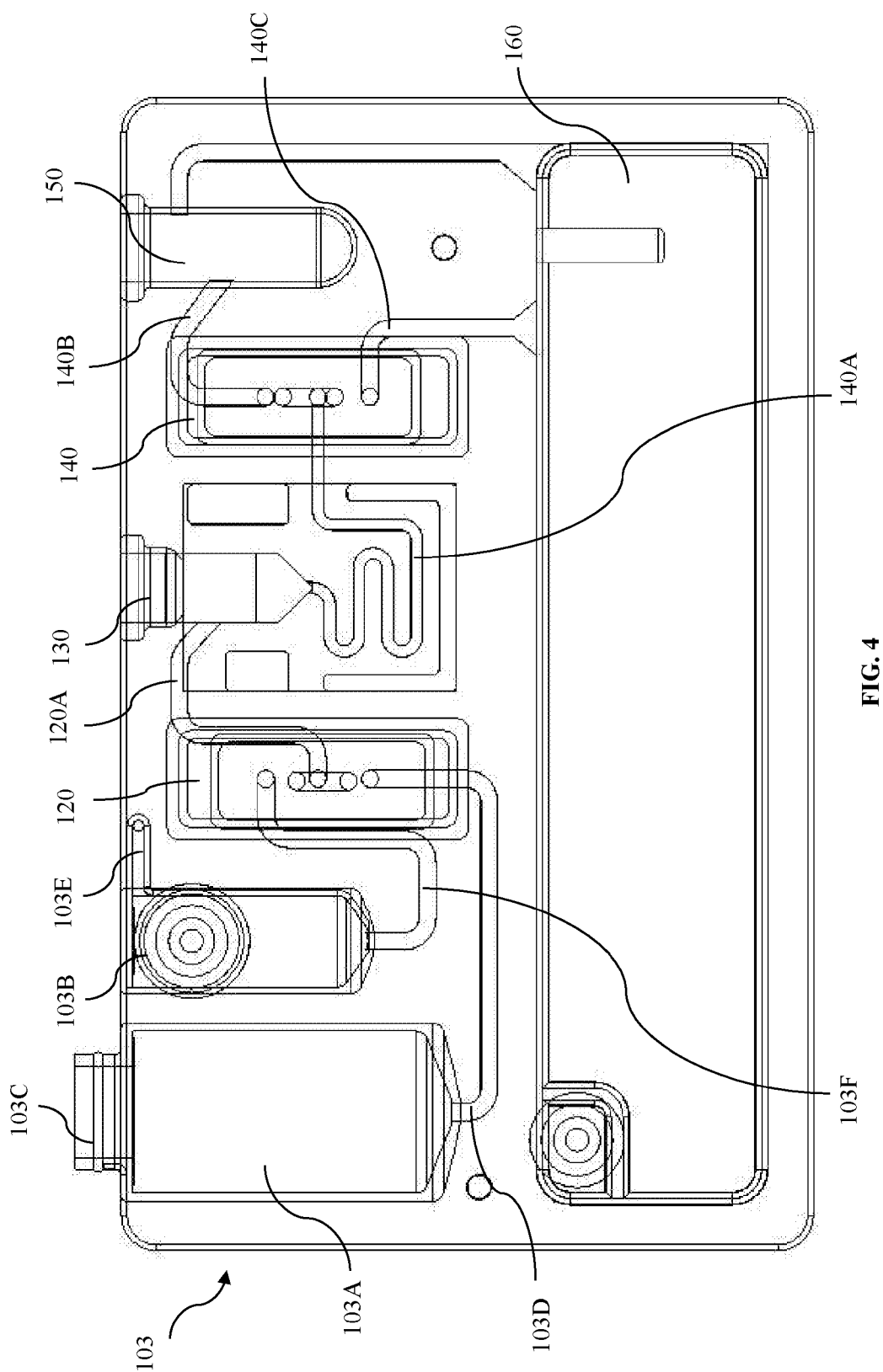

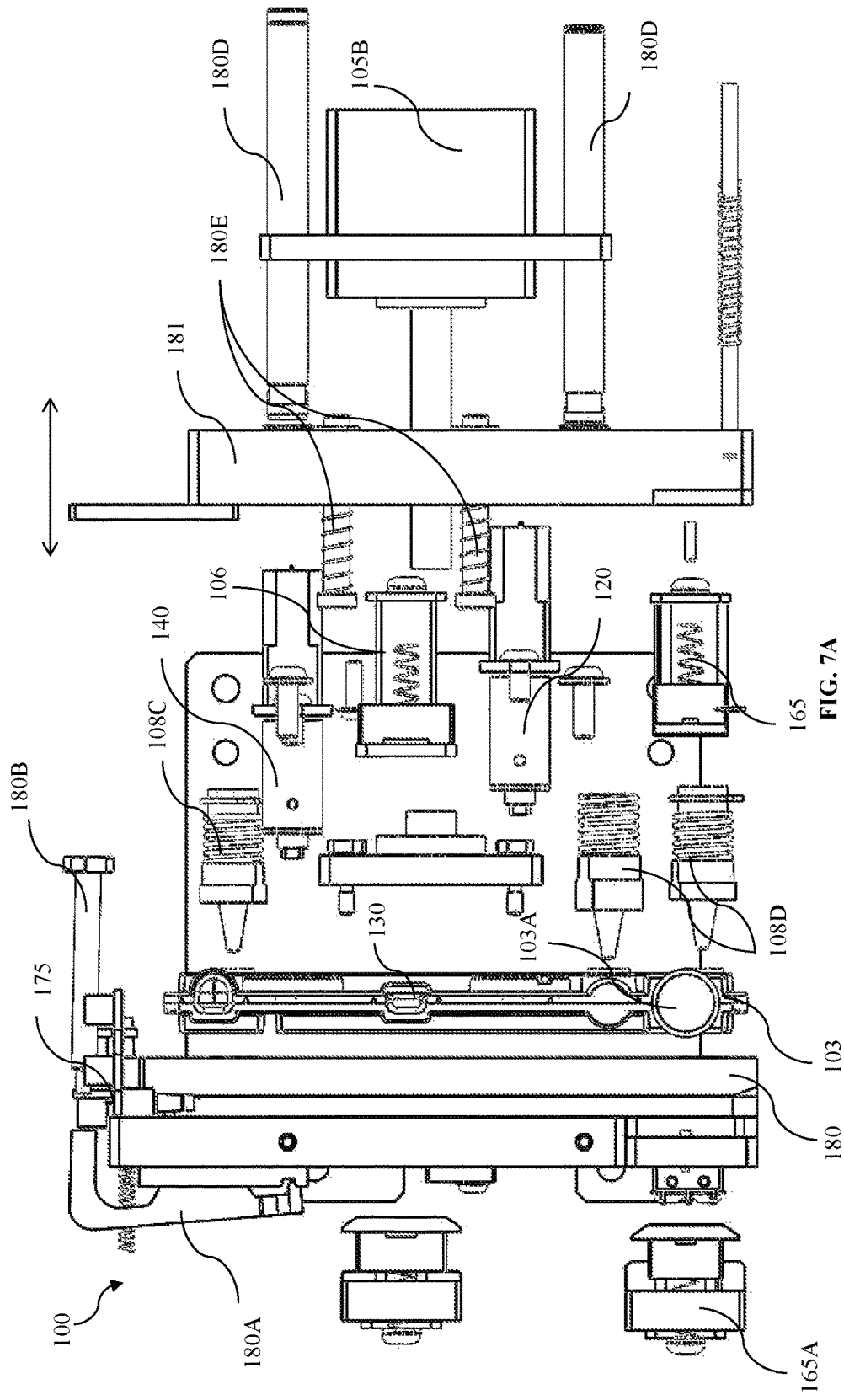

PORTABLE DEVICE FOR PURIFYING BIOLOGICAL SAMPLE AND A METHOD THEREOF

TECHNICAL FIELD

The present disclosure generally relates to field of biomedical sciences. Particularly, but not exclusively the present disclosure relates to devices for purification of biological sample. Further, embodiments of the present disclosure disclose a portable device and a method for purifying the biological sample.

BACKGROUND

Biological samples such as blood samples, sputum sample, etc. may be subjected to different analysing and processing steps for detection of one or more ingredients like microbes. Detection of such ingredients proves to be one of the important steps in sample analysing and processing, since qualitative and quantitative detection of the ingredients provides indication relating to various effects of the sample with the biological and non-biological matters in which they are present. For example, if a particular microbe is present in a given biological sample and the microbe tends to contaminate the sample leading to various diseases, then qualitative and quantitative detection and analysis of microbes is essential. Qualitative analysis involves determining nature and characteristics of the microbe, while quantitative analysis involves determination of quantity or concentration of the microbe present in given volume/mass of the sample. Both qualitative and quantitative analyses are crucial to prevent or treat the disease. On the other hand, processing of samples involves purification of the sample which is one of the important steps in processing stage. Purification usually involves separation or isolation of one or more target particles/constituents from rest of the components in the sample by chemical, electrical, mechanical, thermal and optical techniques.

Conventionally, while performing analysis and processing of biological samples, the samples are collected from the subject, optionally stored under appropriate conditions, and are subjected to various tests for identification of constituents and ingredients present in the sample. The existing processes and techniques for analysis involve multiple steps performed sequentially, and are usually time consuming. In addition, the known analysing processes are complex, require expensive set-ups and equipments, require sophisticated and controlled laboratory conditions, continuous supply of electricity, as well as highly skilled and trained professionals. For example, in Polymerase Chain Reaction process where one or more copies of De-oxy Ribo Nucleic acids (DNAs) are amplified to several orders of magnitude to generate thousands to millions of copies of DNA sequences. In such techniques, highly skilled operators, technical experts and sophisticated laboratories maintained under controlled conditions are required. Similarly, to carry out purification of the nucleic acid sample, the above mentioned conditions are required. Conventionally, different methods or techniques are used for nucleic acid sample purification. One of such conventional techniques uses robot based pipetting stations with commercial nucleic acid extraction reagent kits, but replaces the user with a robot (x-y-z motion station) that does all pipetting activities. These are huge, non-movable systems meant for high throughput labs, which runs on AC mains. Samples need to be batched to run. So these systems are not suitable for low scale sample analysis and processing application. Also, in some of the conventional arts, a fully automated machine is disclosed, which is designed to purify plasmid DNA from recombinant bacteria. This machine is essentially an electronically controlled mechanical robot which performs multiple small scale plasmid purifications. The machine utilizes a precision centrifuge, with sets of disposable plastic tubes into which starting bacterial-cultures are placed. Robotic pipet holders positioned above the centrifuge introduce and remove fluids from disposable sample tubes during the run, which involves centrifugation of the samples at two different steps or cycles. This machine can purify up to twelve samples of plasmid DNA in less than an hour. However, the machine is extremely expensive for laboratory use. Some of the other types of conventional techniques use magnetic nano-particle (MNP) based system which binds and extracts nucleic acids. The system utilizes mechanical systems that are cumbersome, and runs on AC mains. Also, batching of samples is required to run 4, 8 or 16 samples at a time, similar to robot based sample analysis. MNPs are usually placed in mid-sized labs with skilled user for loading liquid reagents.

Apart from nucleic acids, several other types of biological samples are analysed and processed for detection of microbes which initiate several diseases in living cells. For example, a sputum sample is analysed and processed to detect microbes which instigate diseases like tuberculosis in living cells. Two of the extensively used techniques are culture testing and smear testing. Culture testing used for the detection of Tuberculosis (TB) and other such infections is time consuming, and the equipment required for conducting such tests use specialized labs having controlled temperature settings. However, this type of culture testing used in the detection of Tuberculosis (TB) and other such infections are limited to laboratories, and are not available to common population or people who are residing in remote locations. The second technique i.e. smear testing is the most commonly employed test and is relatively inexpensive than the culture test. However, it has disadvantages such as low sensitivity, low accuracy or inaccuracy with respect to detection of microbes causing Tuberculosis (TB).

In the light of the foregoing discussion, there is a need for improved portable device for purifying biological samples to overcome one or more limitations stated above.

SUMMARY OF THE DISCLOSURE

One or more shortcomings of conventional systems or devices are overcome and additional advantages are provided through the provision of system or device as claimed in the present disclosure. Additional features and advantages are realized through the techniques of the present disclosure. Other embodiments and aspects of the disclosure are described in detail herein and are considered a part of the claimed disclosure.

In one non-limiting embodiment of the present disclosure, there is provided a portable device for purifying biological sample. The device comprises a housing and a cartridge holder accommodated in the housing for holding at least one cartridge. The at least one cartridge is configured to purify the biological sample. At least one pump is positioned in the housing which is fluidly connectable to the at least one cartridge and is configured to circulate the biological sample and one or more fluids through the at least one cartridge. Further, at least one heating element is configured in the housing to selectively heat a matrix chamber in the at least one cartridge. The device also comprises at least one actuator disposed in the housing which is configured to actuate one or more valves in the at least one cartridge to selectively route the biological sample and the one or more fluids in the at least one cartridge. Further, the device comprises a control unit interfaced with the at least one actuator, the at least one heating element and the at least one pump. The control unit is configured to regulate operation of the at least one actuator, the at least one pump and the at least one heating element during purification of the biological sample.

In an embodiment of the present disclosure, the matrix chamber comprises matrix selected from a group comprising cotton, derivatives of cotton and synthetic polymers having blends of cotton or any combination thereof.

In an embodiment of the present disclosure, the cotton is selected from a group comprising natural cotton, surgical cotton, clinical grade cotton, commercial cotton, spun cotton, water washed cotton, acid or base washed cotton, autoclaved cotton, buffer treated cotton having pH ranging from about 1 to about 14, salt solution treated cotton, organic solvent treated cotton, pressed cotton and processed cotton.

In an embodiment of the present disclosure, the one or more fluids are at least one of one or more buffer solutions, one or more reagent solutions, at least one elute material and at least one waste fluid.

In an embodiment of the present disclosure, the at least one cartridge comprises at least one first chamber to hold the biological sample, and at least one second chamber configured to receive and hold the one or more reagent solutions.

In an embodiment of the present disclosure, the biological sample is selected from a group comprising, but not limiting to blood, plasma, sputum, serum, saliva, urine, cell extracts or tissue extracts, as well as samples collected using swabs.

In an embodiment of the present disclosure, at least one container is configured in the housing to hold the one or more buffer solutions.

In an embodiment of the present disclosure, the device comprises at least one reagent holding unit disposed in the housing.

In an embodiment of the present disclosure, the at least one actuator comprises a first actuator configured to operate a first valve of one or more valves to selectively allow flow of the biological sample and one or more reagent solutions through the matrix chamber.

In an embodiment of the present disclosure, the at least one actuator comprises a second actuator configured to operate a second valve of the one or more valves to selectively allow flow of at least one elute material from the matrix chamber to at least one elute collection chamber, and at least one waste fluid from the matrix chamber to at least one dump chamber.

In an embodiment of the present disclosure, the one or more valves are two position, three-way directional control valves and flow control valves.

In an embodiment of the present disclosure, the at least one actuator actuates the one or more valves between a first position and a second position.

In an embodiment of the present disclosure, the at least one elute material is nucleic acid.

In an embodiment of the present disclosure, the nucleic acid is selected from a group comprising, but not limiting to DNA, RNA and PNA.

In an embodiment of the present disclosure, the at least one pump is configured to maintain a differential fluid pressure in the at least one cartridge to enable flow of the biological sample and the one or more fluids through the at least one cartridge.

In an embodiment of the present disclosure, the control unit is configured to selectively operate a combination of the at least one pump and the at least one actuator, and the at least one heating element.

In an embodiment of the present disclosure, the at least one pump, the at least one heating element and the at least one actuator are powered by a battery configured in the device.

In an embodiment of the present disclosure, the device comprises a plurality of sensors configured to detect a plurality of process parameters inside the device, the process parameters are at least one of temperature of the matrix chamber, pressure of the biological sample and the one or more fluids, positions of the one or more valves, and presence of the at least one cartridge.

In another non-limiting embodiment of the present disclosure, there is provided a method for purifying biological sample. The method comprises acts of, operating, by a control unit, at least one actuator to actuate one or more valves configured in at least one cartridge to selectively allow flow of the biological sample and one or more reagent solutions into a matrix chamber of the at least one cartridge. The at least one actuator and the one or more reagent solutions are disposed in a housing of a device. Further, the method comprises activating, by the control unit, at least one heating element for heating the matrix chamber to isolate at least one nucleic acid in mixture of the biological sample and the one or more reagent solutions. The at least one heating element is configured in the housing of the device. Furthermore, the method comprises of operating, by the control unit, the at least one actuator to actuate the one or more valves in the cartridge to selectively allow flow of the at least one fluid from the matrix chamber.

In an embodiment of the present disclosure, the at least one nucleic acid fluid is routed into an elute collection chamber, and the waste fluids are routed into a dump chamber.

In an embodiment of the present disclosure, the method comprises act of operating, by the control unit, at least one pump to maintain a differential fluid pressure in the at least one cartridge to enable flow of the biological sample, and the one or more reagent solutions.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The disclosure itself, however, as well as a preferred mode of use, further objectives and advantages thereof, will best be understood by reference to the following detailed description of an illustrative embodiment when read in conjunction with the accompanying drawings. One or more embodiments are now described, by way of example only, with reference to the accompanying drawings wherein like reference numerals represent like elements and in which:

FIG. 4 illustrates schematic front view of the disposable cartridge used in the device of FIG. 1, according to an embodiment of the present disclosure.

FIGS. 7A and 7B illustrate exploded top view and exploded perspective view respectively of a docking mechanism provided in the device of FIG. 1, according to an exemplary embodiment.

Figure 1:
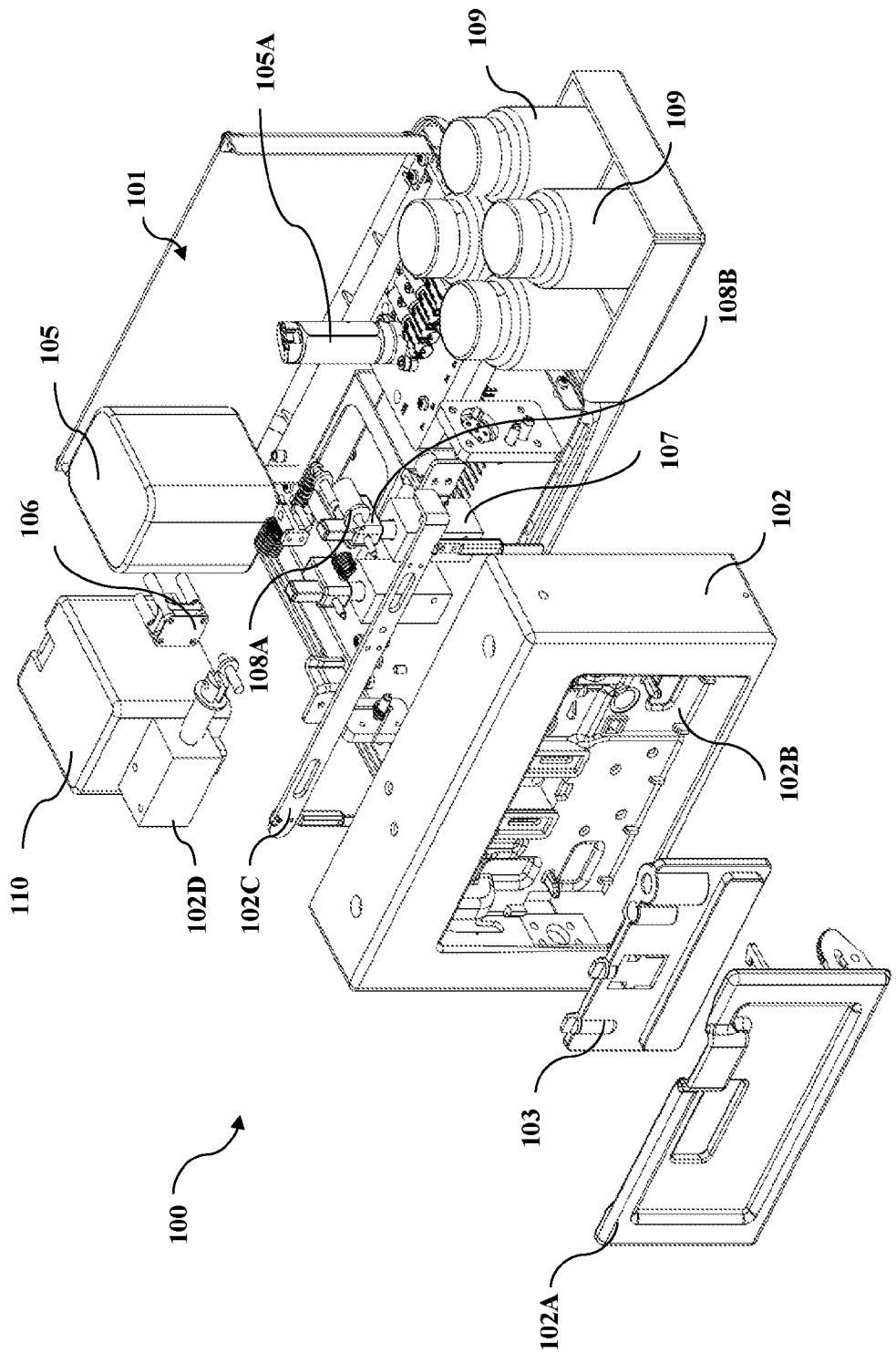
FIG. 1 illustrates exploded perspective view of a device for purifying biological samples, according to an embodiment of the present disclosure.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

The foregoing has broadly outlined the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the scope of the disclosure as set forth in the appended claims. The novel features which are believed to be characteristic of the disclosure, as to its assembly, together with further objects and advantages will be better understood from the following description when considered in connection with the accompanying figures. It is to be expressly understood, however, that each of the figures is provided for the purpose of illustration and description only and is not intended as a definition of the limits of the present disclosure.

To overcome one or more limitations stated in the background, the present disclosure provides a portable device for purifying biological sample, such as but not limiting to blood, sputum, urine, cells, tissues etc. containing genetic materials such as nucleic acids. The portable device comprises a housing to enclose or house all the components constituting the device. The housing serves as base structure for supporting the components on it. The housing accommodates at least one cartridge holder which holds one or more cartridges. The one or more cartridges may be removably accommodated in the cartridge holder, and are configured to purify the biological sample. In an embodiment of the present disclosure, the cartridge is a disposable cartridge. The term "disposable" indicates that the cartridge can be discarded or disposed-off upon one or more usage cycles. In one embodiment, the cartridge is configured as an assembly having plurality of components inter-connected and assembled within it. The components in the cartridge take part in transportation, handling, storage and processing of biological sample and one or more fluids. This indicates that the purification of biological sample takes place in the presence of the one or more fluids, such as one or more buffer solutions and reagent solutions. The housing also comprises one or more pumps fluidly disposed in communication with the cartridge. The pump is configured to circulate the biological sample and the one or more fluids inside the cartridge. The pump is disposed inside the device for maintaining pressure differences in flow lines required to circulate the biological sample and the one or more fluids.

The device further comprises at least one heating element positioned in the housing to heat a matrix chamber of the cartridge. The matrix chamber is provided in the cartridge to thermally isolate at least one elute material from the biological sample. The term "elute material" or alternatively referred to as "elute" refers to target ingredient in the biological sample that needs to be extracted and separated from rest of the biological sample. In an embodiment, the elute material is nucleic acids. The rest of the sample that is separated from elute material is referred to as waste fluids throughout the detailed description. The matrix chamber mentioned above isolates the elute materials from the biological sample in the presence of heat dissipated by the heating element. Further, the device comprises one or more actuators that take part in actuating one or more valves present inside the cartridge. The one or more valves are configured to selectively direct flow of biological sample and one or more fluids into the matrix chamber, as well as out of the matrix chamber. In an embodiment of the present disclosure, the one or more valves comprise a first valve and a second valve. The first valve is disposed between at least one first chamber containing the biological sample and the matrix chamber. In addition, the first valve fluidly connects at least one second chamber containing one or more reagent solutions with the matrix chamber. On the other hand, the second valve fluidly connects the matrix chamber separately with an elute collection chamber and a dump chamber. The second valve selectively allows flow of elute materials from the matrix chamber into the elute collection chamber, and flow of waste fluids from the matrix chamber into the dump chamber. The actuators described above are configured to actuate the one or more valves comprising first and second valves between first and second positions. In an embodiment, the actuators are solenoid based actuators and one or more valves are solenoid based actuator driven valves. In another embodiment, the valves are two-position, three-way directional and flow control fluid valves. The first and second chambers disclosed above are fluidly connected to the matrix chamber by the first valve.

The term fluidly connected used herein above and below refers to a connection between the two fluid carrying units or media in the form of channels or passages which enable movement of fluids.

The portable device of the present disclosure further comprises a control unit interfaced with the pump, the heating element and the actuators. The control unit is configured to regulate operation of each of the pump, the actuator and the heating element to obtain desired operational characteristics during the purification of biological sample. The device is also configured with a plurality of sensors to sense or detect a plurality of process parameters, such as but not limited to temperature of the matrix chamber, pressure of the biological sample and the one or more fluids, positions of the one or more valves, and presence of the at least one cartridge inside the device. The control unit receives signals from the plurality of sensors to regulate different process parameters inside the device to achieve desired process conditions inside the device. A power source such as a battery is also provided in the device to supply power necessary for the operation of the pump, the heating element, the actuators and the sensors.

In another embodiment of the present disclosure, there is provided a method for purifying biological sample. The method comprises acts of, operating by a control unit, at least one actuator to actuate one or more valves configured in at least one cartridge. The actuation of the one or more valves selectively allows flow of the biological sample and one or more reagent solutions into a matrix chamber of the cartridge. The method further comprises act of activating, by the control unit, at least one heating element for heating the matrix chamber. Heating of the matrix chamber isolates nucleic acids in a mixture of the biological sample and the one or more reagent solutions contained in the matrix chamber. This is followed by act of operating the at least one actuator by the control unit to actuate the one or more valves to selectively allow flow of one or more fluids out of the matrix chamber to separate chambers. The method further comprises act of operating one or more pumps before the actuation of the actuator. The pump is configured to maintain differential pressure across the cartridge to enable circulation of the biological sample & reagent solutions. The elute fluid is routed into a elute collection chamber from the matrix chamber, and the waste fluids are routed into a dump chamber from the matrix chamber, all of which are present inside the cartridge.

The terms "comprises", "comprising", or any other variations thereof used in the specification, are intended to cover a non-exclusive inclusion, such that a system or a device comprises a list of components or steps does not include only those components or steps but may include other components or steps not expressly listed or inherent to such setup. In other words, one or more elements in a system or a device or an apparatus proceeded by "comprises . . . a" does not, without more constraints, preclude the existence of other elements or additional elements in the system or apparatus.

FIG. 1 is an exemplary embodiment of the present disclosure which illustrates exploded perspective view of the device (100) used for purifying biological sample, including but not limited to blood, serum, sputum, urine, stool, cells, tissues and the like. The purification of biological samples involves separation or isolation of target materials or fragments from rest of the constituents of the sample. For example, nucleic acid analysis involves separation of nucleic acids comprising DNAs or RNAs or PNAs from biological samples such as cells and tissues, and subjecting the isolated nucleic acids to further processing techniques like Polymerase Chain Reactions (PCR), preferably real-time PCR (qPCR), by employing a commercial thermal cycler such as ABI 7500 (Applied Biosystems). Details pertaining to the real-time PCR, PCR mix and PCR reaction conditions, can be thoroughly understood as carried out in US patent publications US 2011/0306046, US 2012/0045761, WO 2012/095714 and PCT/IB2013/000371 for probes and primers for detection of Malaria, Chikungunya, Typhoid and Tuberculosis respectively. The separation can be carried out through physical separation methods like electric separation, electro-chemical separation, optical techniques, thermal techniques and the like. The target materials can also be isolated from the samples by some chemical methods, including chemical treatments using one or more reagents, titrations. The device disclosed in embodiments of the present disclosure relates to isolation of target materials from biological samples by employing one or more isolation techniques mentioned above, which will be explained in detail in forthcoming paragraphs of the detailed description.

Particularly, the isolated and purified nucleic acid obtained from the biological samples post exposure of said biological samples to the matrix in the cartridge housed in the devise of the present disclosure is subjected to real-time PCR processing to assess and quantify specific microbial contamination/infection. Said PCR processing involves employing a PCR reaction mixture comprising nucleic acid amplifying reagents, primers and probes specified in aforementioned patent applications directed for identifying infections such as Malaria, Chikungunya, Typhoid and Tuberculosis etc. The PCR mixture optionally also comprises cofactors, reaction buffers, sterile water and a mixture of deoxy-ribo-nucleotide triphosphate (dNTP) or a combination thereof. The processing specifically involves contacting the purified biological sample (obtained by employing the device of the present disclosure) with said reaction mixture in a thermal cycler and amplifying the nucleic acid to obtain copies of target sequence therein and identifying the target sequence by detecting increased fluorescence levels during the PCR reaction. The amplification is measured in terms of increase in fluorescence signal and the amount of signal produced is compared with a standard curve to derive the amount of DNA present in the original sample. Therefore, the device of the present disclosure can be employed for identification and quantification of infections such as, but not limiting to Malaria, Chikungunya, Typhoid and Tuberculosis, in any aforementioned biological samples. The Application of the present device in identifying and quantifying microbial infection is not limited to Malaria, Chikungunya, Typhoid and Tuberculosis alone, but can be extended to other bacterial, viral or protozon caused infections/diseases as well.

Referring to FIG. 1, the portable device (100) comprises of a housing (101) configured to enclose components that are involved in purification of biological sample. The housing (101) typically resembles a casing or an enclosure and serves as basic structure for holding and supporting the components constituting the portable device (100). In an embodiment of the present disclosure, shape of the housing (101) is at least one of, but not limited to square, rectangular, cylindrical, or any other shape which is known in the art. Further, the material used to devise the housing (101) is selected from at least one of metals, metal alloys, plastic, polymers, composite materials or any other materials which offer desired properties and durability to the device (100). The housing (101) comprises a provision for removably accommodating a cartridge holder (102). The cartridge holder (102) in turn can accommodate a cartridge (103) within it. The cartridge (103) is a unit disposable inside the device (100) where purification of biological sample takes place, and all the other components present in the device (100) perform one or several operations that constitute one or more steps of the purification process. The cartridge holder (102) which resides in the housing (101) comprises a cartridge housing recess (102B) formed on one of the sides or surfaces of the holder (102). The side or surface of cartridge holder (102) where the recess (102B) is formed is provided with a cartridge loading door (102A) which is configured to selectively close the recess (102B). The cartridge loading door (102A) provides access to the recess (102B) where cartridge (103) is positioned for carrying out sample purification. The cartridge loading door (102A) also allows the user to load the cartridge (103) inside the recess (102B), as well as to unload or remove the cartridge (103)

from the recess (102B) for disposing-off. In an embodiment of the present disclosure, the cartridge loading door (102A) is hingedly connected to a bottom end of the cartridge holder (102), as shown in FIG. 1. Further, a slider latch assembly (102C) provided with a latch release mechanism and operated by a mechanism (102D), including but not limited to solenoid mechanism. The slider latch assembly (102C) with the mechanism (102D) is provided on top of the cartridge holder (102) for locking and unlocking the cartridge loading door (102A) with the holder (102) for the purposes of loading and unloading the cartridge (103).

The portable device (100) further comprises at least one reagent holding unit (109) which can receive and store one or more reagents. The reagents stored in the reagent holding unit (109) are supplied into the cartridge (103) to facilitate purification of the biological sample. The reagent holding unit (109) allows the user or operator to dispense desired reagents into it, depending on the type of biological sample selected for purification. In an embodiment of the present disclosure, the reagent holding unit (109) is cylindrical in shape resembling a bottle. The reagent stored in the reagent holding unit (109) is supplied into the cartridge (103) by fluid handling manifold (104) provided in the device (100). The fluid handling manifold (104) is provisioned with an auxiliary pump (105A) and one or more auxiliary valves (AV) which establish fluid communication between the reagent holding unit (109) and the cartridge (103). The auxiliary pump (105A) and one or more auxiliary valves (AV) take part in discharging the reagent stored in the reagent holding unit (109) into the cartridge (103). In an embodiment of the present disclosure, the auxiliary pump (105A) includes but not limiting to electric, hydraulic, solenoid and pneumatic pumps driven by a motor. In another embodiment, the auxiliary valves (AV) include but not limited to directional, flow and pressure control valves such as but not limited to two way, three way—multiple position directional control valves, pressure reducing and pressure relief valves and needle type flow control valves. Apart from handling the reagent solution stored in the reagent holding unit (109), the fluid handling manifold (104), along with auxiliary pump (105A) and valves (AV), is configured to fluidly connect the cartridge (103) with other elements of the device (100). The "fluid handling manifold" herein above and below refers to flow lines configured in the device (100) which allows circulation or flow of one or more fluids inside the device (100), including into the cartridge (103).

Figure 7B:
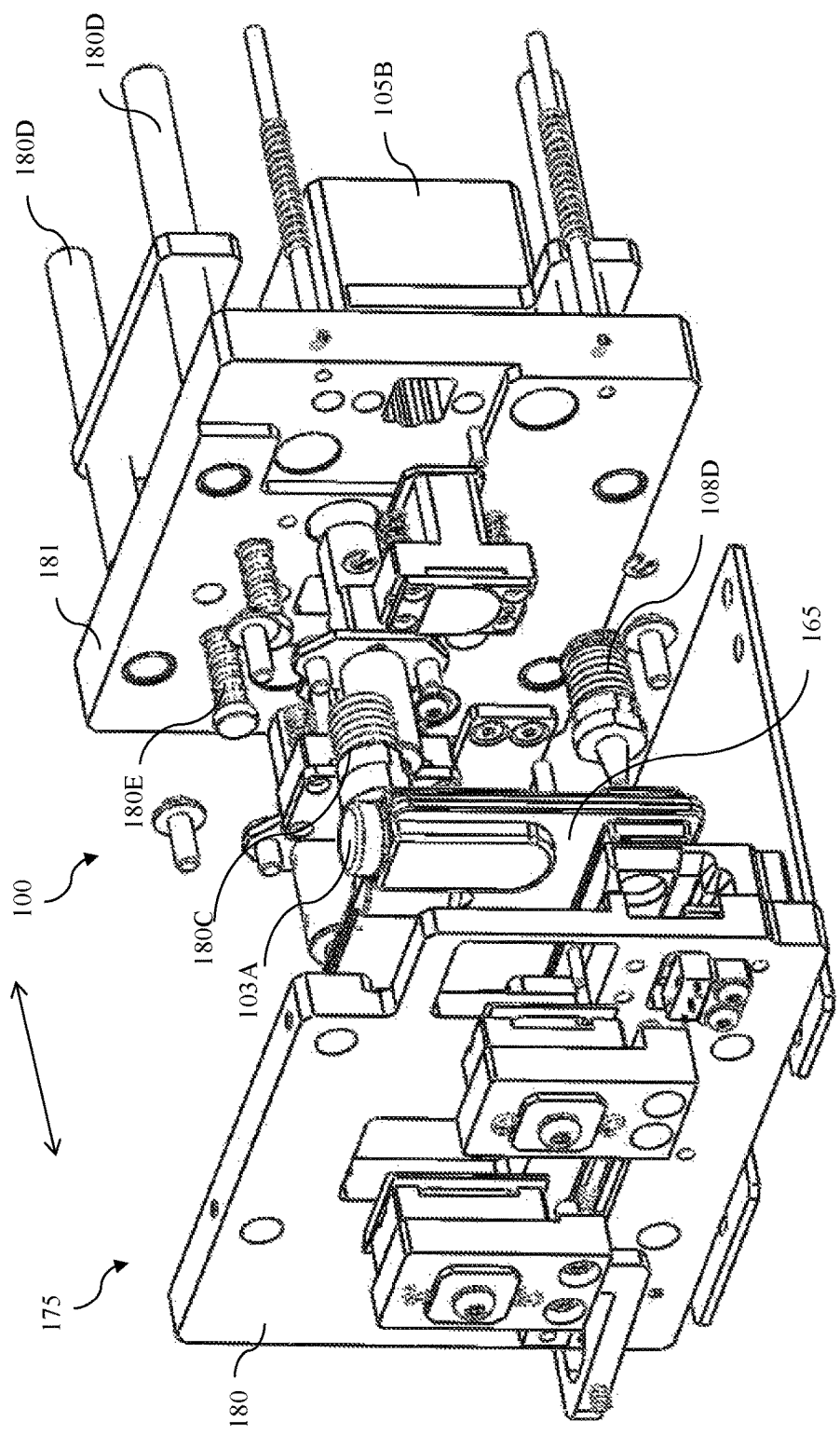

The portable device (100) of the present disclosure also comprises one or more heating elements (106) configured in the housing (101) proximal to the cartridge (103). The heating element (106) is positioned inside the housing (101) such that a thermal contact is established between the heating element (106) with a matrix chamber (130) of the cartridge (103). In an embodiment of the present disclosure, the heating element (106) is positioned proximal to the matrix chamber (130) of the cartridge (103) for heating the matrix chamber (130) and maintaining desired temperature in it. In another embodiment of the present disclosure, the heating element (106) is positioned in the housing (101) in such a way that it comes in contact with the matrix chamber (130) for heating and maintaining desired temperature in it. In former configuration, heat transfer takes place from the heating element (106) to the matrix chamber (130) by conduction and/or radiation, and in latter configuration, heat transfer is through conduction, convection or radiation. The heat dissipated by the heating element (106) maintains the matrix chamber (130) at desired temperature range to facilitate the purification process of the sample. The temperature range is different for different samples, and the heating element (106) is adapted to meet a range of temperature requirements in the matrix chamber (130). In an embodiment of the present disclosure, the heating element (106) is an electric based heating element including but not limited to resistive, conductive and inductive type heating element. In an alternate embodiment of the present disclosure, the heating element (106) is configured as a heater assembly in which one or more thermally sensitive conducting elements are assembled and electrically interfaced to generate and dissipate heat. The heat so dissipated is utilized in maintaining required temperature in the matrix chamber (130) during purification of the sample. In an embodiment of the present disclosure, the heating element (106) is a thin film ceramic based heating element which uses electric power from the battery (110) to dissipate heat to the matrix chamber (130). In an exemplary embodiment of the present disclosure, a sample heating unit (165, 165A) is provisioned in the device (100) proximal to or in contact with the first chamber (103A) containing the biological sample, as shown in FIGS. 7A and 7B. The sample heating unit (165, 165A) comprises a sample heating element (165) and a holder (165A) to hold the sample heating element (165) inside the device (100). The sample heating element (165) dissipates heat into the first chamber (103A) to heat the biological sample to a predefined temperature range. The pre-heating of the biological sample before letting it into matrix chamber (130) enhances characteristics such as but not limited to on-board lysis of the biological sample, particularly in case of the samples from which nucleic acids (DNA and RNA) are extracted. In an alternate embodiment, the biological sample along with one or more buffer solutions is heated by the sample heating unit (165, 165A). The sample heating unit comprising sample heating element (165) and holder (165A) is shown in FIGS. 7A and 7B.

Further, the portable device (100) comprises one or more actuators (107) disposed in the housing (101) for actuating one or more valves (V) provided in the cartridge (103). The one or more actuators (107) are positioned in the housing (101) such that they are adjacent or proximal to the cartridge (103) when the cartridge (103) is loaded and locked inside the cartridge holder (102). This arrangement in which the one or more actuators (107) are positioned proximally to the cartridge (103) allows external interfacing of the actuators (107) with the one or more valves (V) of the cartridge (103) to allow flow of the biological sample and one or more fluids in the cartridge (103). The actuators (107) are configured to selectively actuate the one or more valves (V) of the cartridge (103), and thereby facilitate in formation of selective paths for flow of the biological sample and the one or more fluids in the cartridge (103). In an embodiment of the present disclosure, the actuators (107) include but not limited to electro-mechanical actuators such as solenoid based actuators and hydraulic actuators. In an embodiment, the actuators (107) are linear actuators including but not limited to piston cylinders, lead-screw mechanisms and the like which use mechanical, electrical, hydraulic and pneumatic power. The linear actuators linearly actuate the first and second valves (120, 140) in the cartridge (103) between first and second linear positions. In another embodiment of the present disclosure, the one or more actuators (107) comprising the first and second actuators (107A and 107B) are rotary actuators including but not limited to electric motors. If the valves (V) comprising first valve (120) and the second valve (140) inside the cartridge (103) are rotary valves, then the actuators (107) comprising first and second actuators (107A, 107B) which respectively operate the first and second valves (120, 140) are rotary actuators, such as servomotors, stepper motors, DC and AC motors optionally with gear drives for power transmission. The device (100) is further configured with at least one first flow element (108A) and at least one second flow element (108B). The flow elements (108A, 108B) fluidly connect the pump (105) with the valves (V) of the cartridge (103). In an embodiment of the present disclosure, the first flow element (108A) is a first nozzle including but not limited to injection nozzle configured to apply fluid pressure to facilitate flow of the biological sample and one or more fluids in the cartridge (103). In another embodiment of the present disclosure, the second flow element (108B) is a second nozzle configured to induce suction pressure or negative pressure to facilitate flow of one or more fluids and the biological sample in the cartridge (103). The first flow element (108A) and the second flow element (108B) may be configured to operate interchangeably in the device (100), and the above mentioned functionalities of flow elements (108A, 108B) should not be construed as limitations on the present disclosure. In an embodiment of the present disclosure, the first and second nozzles (108A, 108B) are pressure inducing and pressure reducing nozzles. Reference is made to FIGS. 7A and 7B to illustrate an exemplary nozzle arrangement in which two nozzles (180D) dock to the bottom part of the cartridge (103) to circulate air within the cartridge (103) to drive the biological sample one or more fluids through channels and chambers inside the cartridge (103). In addition, a single nozzle (108C) which is docked to the top part of cartridge (103) is configured to deliver process liquids (such as reagent solutions contained in holding unit (109)) in the device (100) into the cartridge (103), through the fluid flow manifold (104). The nozzles (108C, 108D) are fluidly connected to the auxiliary pump (105A) which enables circulation of the fluids mentioned above.

Figure 2:
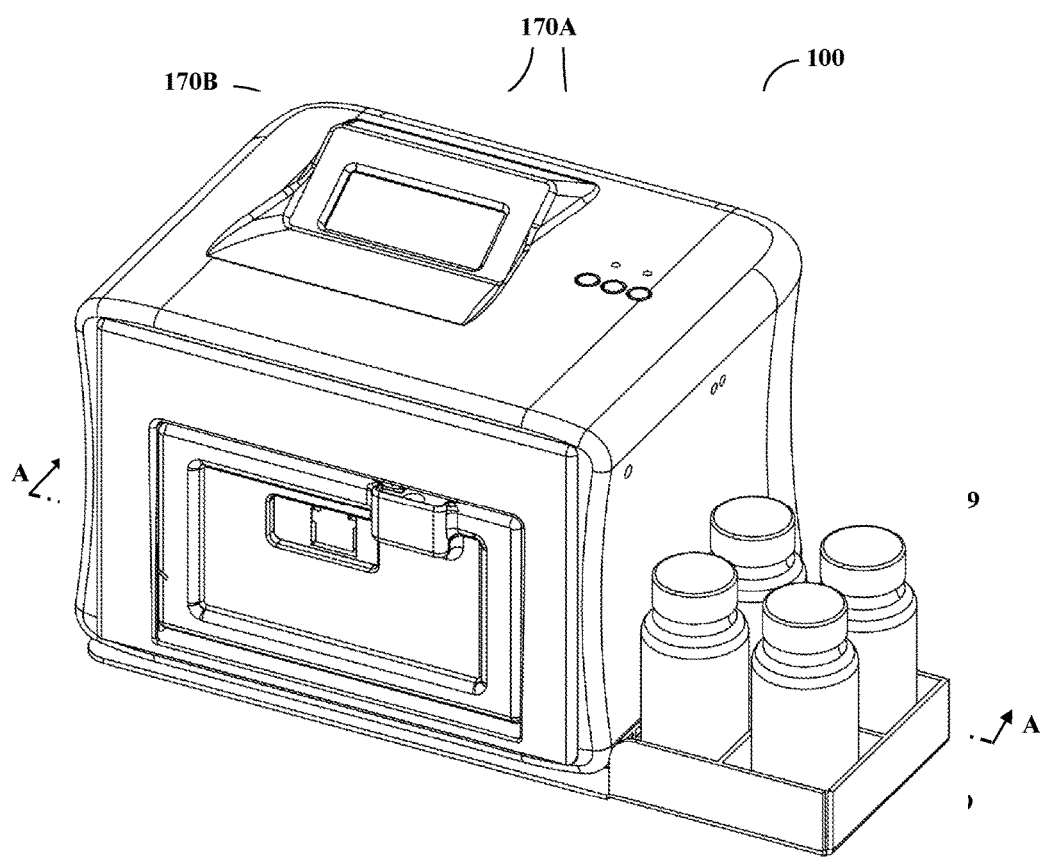
FIG. 2 illustrates assembled perspective view of the device of FIG. 1.

FIG. 2 is an exemplary embodiment of the present disclosure which illustrates perspective view of the device (100) for purifying biological samples. Reference is made to FIG. 1 along with FIG. 2 throughout this section. The portable device (100) of the present disclosure comprises a user-interface (170) comprising an input interface (170A) which allows the user to operate and input various input parameters to the device (100). The input interface (170A) comprises a power button used to turn ON and turn OFF the device (100) and an eject button to eject the cartridge loading door (102A) outside the cartridge holder (102) for loading and unloading the cartridge (103). In addition, the input interface (170A) comprises a third button namely a run button which starts the sample purification process inside the device (100). The input interface may be in the form of an input panel comprising a plurality of buttons mentioned above or in the form of touch panel comprising a plurality of menus that can be touch selected. In an embodiment of the present disclosure, the input panel is a LCD panel or a LED panel comprising a plurality of selection menus for turning ON/OFF, effecting cartridge door ejection and starting the sample purification process. The input panel is connected with the battery source (110) configured in the device (100) and takes power from the battery source (110). Pushing the power button or power menu provisioned in the input interface (170A) allows user to power the components of the device (100) by the battery power, or to disconnect the components from the battery.

The user interface (170) also comprises an output interface which provides information to the user or the operator regarding information related to ongoing process inside the device (100), end result of the process in the form of message to notify the user to take out the cartridge to obtain the purified sample, and operational characteristics of all the components inside the device (100). For example, the output interface (170B) can include a display unit including but not limited to 2-line LCD display which provides information such as status of the run and error messages to the user in case one or more errors are detected during the process. The display is also configured to provide information such as condition of one or more components inside the device (100), for example, charge condition of the battery. This feature allows the user to easily identify if there are any malfunctions in one or more components present in the device (100), so that the user can immediately take measures to attend the malfunctioning issues.

Further the user interface (170) comprising the input interface (170A) and output interface (170B) are associated with a plurality of sensors [not shown] and the control unit (112) configured in the device (100). As soon as the user switches ON the device (100), loads the cartridge (103) and selects the run option, programs stored in the control unit (112) selectively operate the components in the device (100) to perform the purification process in the cartridge (103). Once purification process is complete, the control unit (112) sends signals to the output interface (170B) to provide information relating to completion of purification stage. Apart from this, the control unit (112) in the device (100) can also receive information relating to malfunctioning of any of the components in the device (100), for example, clogging or leakage in the lines of the cartridge (103). Accordingly, the control unit (112) sends signals to notify the user regarding the corresponding malfunction of one or more components. If a malfunction is detected during on-going of the process, the user can abort the process and attend to the identified malfunction, for example, replacing a cartridge whenever a leakage or clog in the cartridge (103) is detected. In addition, a plurality of process parameters detected by the plurality of sensors can also be notified to the user via the control unit (112).

In an embodiment, the control unit (112) is a Microprocessor based control units. One skilled in the art can envisage having a Microcontroller based control unit. The control unit (112) may comprise a central processing unit ("CPU" or "processor"). The processor may comprise at least one data processor for executing program components for executing user or system generated processes. A user may include a person, a person using a device, or such a device itself. The processor may include specialized processing units such as integrated system (bus) controllers, memory management control units, floating point units, graphics processing units, digital signal processing units, etc.

The processing unit may include a microprocessor, such as AMD Athlon, Duron or Opteron, ARM's application, embedded or secure processors, IBM PowerPC, Intel's Core, Itanium, Xeon, Celeron or other line of processors, etc. The processing unit may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc. Further, a microprocessor based control unit encompassing the aforementioned features and several other features is known in the art, and is not covered in detail in the embodiments of the present disclosure.

In some embodiments, the processor may be disposed in communication with one or more input/output (I/O) devices via I/O interface. The I/O interface may employ communication protocols/methods such as, without limitation, audio, analog, digital, stereo, IEEE-1394, serial bus, Universal Serial Bus (USB), infrared, PS/2, BNC, coaxial, component, composite, Digital Visual Interface (DVI), high-definition multimedia interface (HDMI), Radio Frequency (RF) antennas, S-Video, Video Graphics Array (VGA), IEEE 802.n/b/g/n/x, Bluetooth, cellular (e.g., Code-Division Multiple Access (CDMA), High-Speed Packet Access (HSPA+), Global System For Mobile Communications (GSM), Long-Term Evolution (LTE), WiMax, or the like), etc.

In some embodiments, the processor may be disposed in communication with a memory (e.g., RAM, ROM, etc.) via a storage interface. The storage interface may connect to memory including, without limitation, memory drives, removable disc drives, etc., employing connection protocols such as Serial Advanced Technology Attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory may store a collection of program or database components, including, without limitation, user interface application, an operating system, web server etc. In some embodiments, monitoring and control system may store user/application data, such as the data, variables, records, etc. as described in this invention. Such databases may be implemented as fault-tolerant, relational, scalable, secure databases such as Oracle or Sybase.

Figure 3:
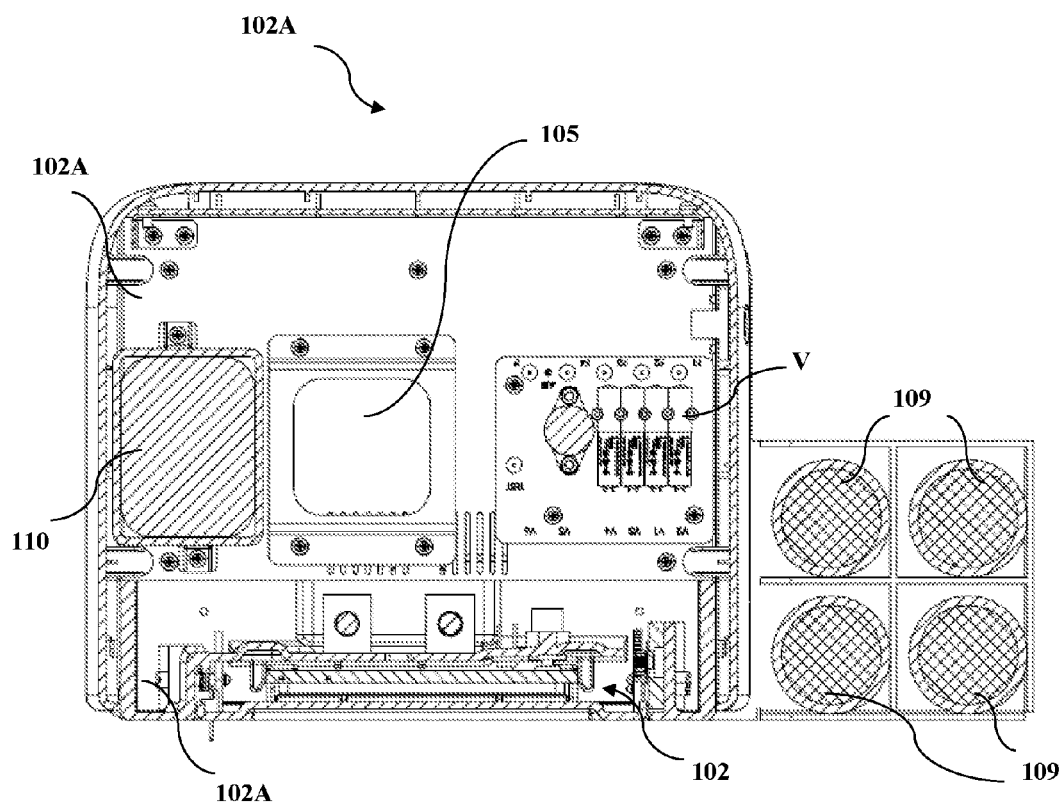
FIG. 3 illustrates sectional top view along A-A of the device shown in FIG. 2.

FIG. 3 is an exemplary embodiment of the present disclosure which illustrates sectional top view along A-A of the device (100) of FIG. 2. Reference is made to FIG. 1 along with FIG. 3 throughout this section. As is seen in FIGS. 1 and 3, the portable device (100) of the present disclosure comprises at least one pump (105) configured to circulate the biological sample into the cartridge (103), and one or more fluids that take part in sample purification to and from the cartridge (103). The pump (105) is adapted to maintain differential pressure across the cartridge (103) to facilitate flow of biological sample and one or more fluids in the cartridge (103). The differential pressure draws the biological sample along with one or more buffer solutions and reagent solutions towards the one or more valves (V) configured in the cartridge (103). On the other end, the differential pressure forces the isolated elute material and waste material into separate collection chambers. In an embodiment of the present disclosure, the pump (105) includes but not limited to stepper motor driven peristaltic pump (105) that can take power from the battery (110) provided in the device (100). The operation of the pump (105) described in this section, and the auxiliary pump (105A) described in previous paragraphs are controlled by the control unit (112). The power requirements of both the pumps (105, 105A) are met by the battery (110) source in the device (100). In an embodiment of the present disclosure, the pump (105), the actuators (107), the valves (V) present in the cartridge (103) and fluid flow lines in the cartridge (103) are fluidly inter-connected and are controlled by the control unit (112).

Further, as shown in FIGS. 1 and 3, the battery (110) of the device (110) which supplies electric power to different components described above is removably accommodated in a compartment [not shown] inside the device (100). The removable accommodation allows battery (110) to be taken out for maintenance and replacement purposes. The battery (110) provisioned in the device (100) is configured to selectively power one component at a time, or a combination of two components at a time. In an embodiment of the present disclosure, the battery (110) is configured to selectively supply power to a combination of pump (105) and actuators (107) in one instance of time, and to the heating element (106) in another instant of time. This selective supply of power minimizes power consumption and reduces electric load on the battery (110). In an embodiment of the present disclosure, the battery (110) includes but not limited to all commercially available electro-chemical based batteries and photo-sensitive cells which comprise an array of photo-voltaic or photo-conductive cells which run on solar power. In another embodiment of the present disclosure, the battery (110) includes but not limiting to rechargeable battery, an array of dry cells, and a power port. The battery (110) is used to supply power to the at least one pump (105), the at least one heating element (106) and the one or more actuators (107).

FIG. 4 is an exemplary embodiment of the present disclosure which illustrates front view of the cartridge (103) which may be removably positioned in the device (100) for purifying the biological sample. The term 'cartridge' is referred to a three dimensional body or a structure of predefined width, length and height and capable accommodating associated components that take part in purification of the biological sample. In an embodiment, the cartridge (103) is a disposable cartridge that can be removably inserted and employed in the device (100) for obtaining purified fragments or genetic materials such as nucleic acids for PCR analysis and detection. In another embodiment, the cartridge (103) is in the form of a disposable cassette. In an embodiment of the disclosure, the cartridge (103) is made of inexpensive and disposable material such as but not limiting to polymeric material selected from polycarbonate or acrylic material or cyclic olefin copolymers or other plastics, which possess good mechanical, thermal and fluidic properties, as well as manufacturability.

As shown in FIG. 4, the cartridge (100) comprises a first chamber (103A) having an inlet port (103C) and an outlet port (103D), and is configured to receive and hold the biological sample that is to be purified with or without one or more buffer solutions. The first chamber (103A) is of a predetermined shape and volume, for receiving adequate quantity of biological sample.

In an embodiment of the present disclosure, the geometry of first chamber (103A) includes but not limiting to cylindrical, rectangular and square or any other geometrical shape, which serves the purpose of receiving and collecting the biological sample. The term 'adequate quantity' herein above and below refers to volume of the biological sample required for obtaining required volume/mass of purified biological sample, to perform further PCR processing, analysis and detection. In an embodiment of the present disclosure, volume of the biological sample added to the first chamber (103A) is in the range of 0.1 ml to about 3 ml. In yet another embodiment, one or more buffer solutions such as dilution buffers may be routed along with the biological sample into the first chamber (103A) based on the biological sample that needs to be purified. The first chamber (103A) is positioned at one extreme end of the cartridge (103) as shown in FIG. 3, according to one embodiment. In another embodiment, the first chamber (103A) can be positioned anywhere in the cartridge (103), to serve the purpose of receiving and holding the biological sample, optionally with one or more buffer solutions. The one or more buffer solutions can be stored in one or more containers [not shown] provided in the device (100), and can be delivered or transported into the first chamber (103A) by auxiliary pump (105A) through fluid handling manifold (104). The first chamber (103A) is further configured with a non-sticking inner surface, so that contents inside it can be drained completely without any residues. Further, the first chamber (103A) is configured with an outlet (103D) for routing either the biological sample or a mixture of biological sample and buffer solutions to the one or more valves (V). The biological sample optionally with the buffer solutions are delivered into the first chamber (103A) through inlet (103C).

Figure 5A:
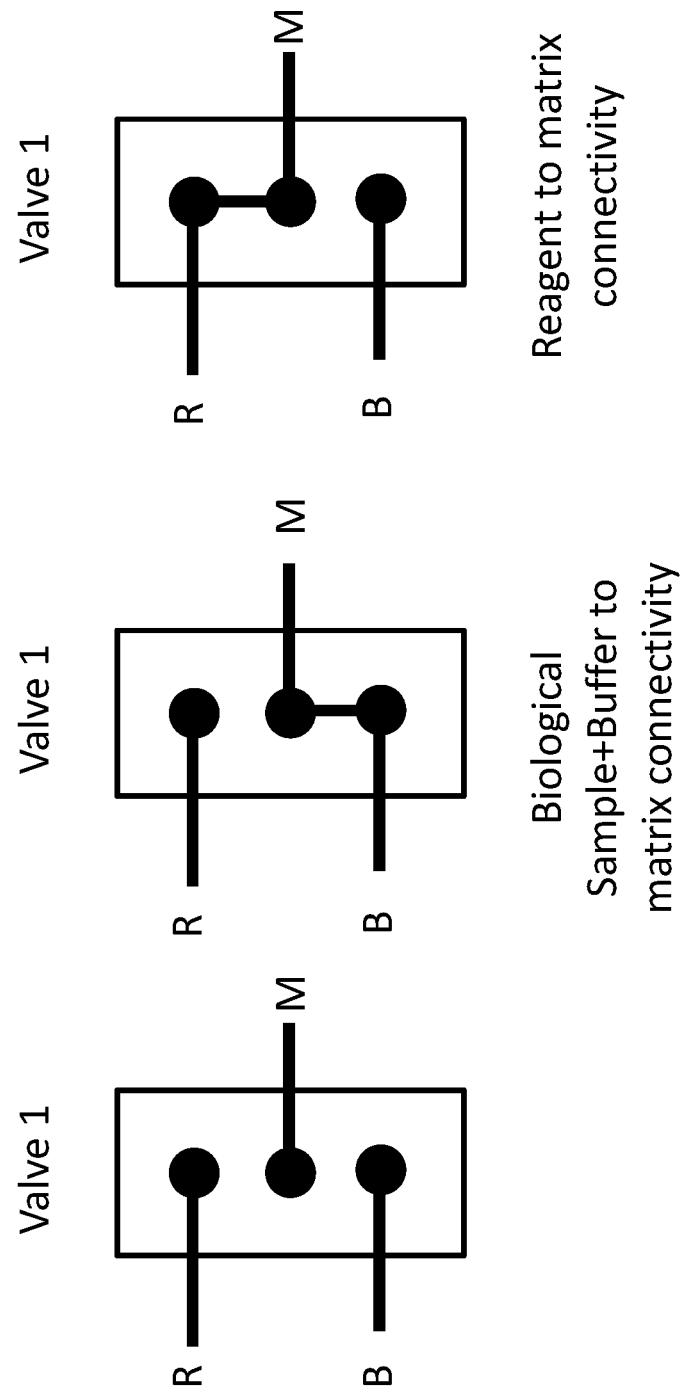
FIG. 5A illustrates schematic diagrams of the first valve actuated between different positions, according to an exemplary embodiment of the present disclosure.

The cartridge (103) also comprises at least one second chamber (103B) having an inlet port (103E) and an outlet port (103F), and is configured to receive and hold reagent solution. The reagent solution is stored in the regent holding unit (109) which is provided in the housing (101) of the device (100) and externally to the cartridge (103). The second chamber (103B) in the cartridge (103) is fluidly connected to the regent holding unit (109) via inlet port (103E), and is capable of receiving one or more reagent solutions added into the reagent holding unit (109) by the operator. The supply of reagent solution from the reagent holding unit (109) into the second chamber (103B) is facilitated by the pump (105), or by the auxiliary pump (105A) in the device (100). In an embodiment, the at least one second chamber (103B) is configured in cylindrical, rectangular, square or other geometric shapes, which serves the purpose of receiving and holding the reagent solution of adequate quantity. In an exemplary embodiment, the volume of the second chamber (103B) is 0.8 ml. the outlet port (103F) is also fluidly connected to one or more valves (V). In an embodiment of the present disclosure, the outlet (103D) of the first chamber (103A) and outlet port (103F) of the second chamber (103B) are fluidly connected to a first valve (120) of the one or more valves (V). The first valve (120) is configured to move to first position (as shown in FIG. 5A) to allow flow of biological sample and buffer solution from first chamber (103A) into the matrix chamber (130), and to second position (as shown in FIG. 5A) to allow flow of one or more reagents into matrix chamber (130) from second chamber (103B). The first valve (120) includes but not limited to two-position, three way directional control valve which allows biological sample with buffer solution into the matrix chamber (130) in one instant, and reagent solution into the matrix chamber (130) in another instant. In an alternate embodiment of the present disclosure, the one or more valves (V) comprising the first valve (120) and the second valve (140) are rotary valves comprising a rotating valve member which allows flow of the biological sample and one or more fluids inside the cartridge (103). The rotary valve members in the rotary valves are actuated between different rotary positions to selectively allow the flow of biological sample and the one or more fluids into the matrix chamber (130), as well as out of matrix chamber (130). In another embodiment of the present disclosure, the valves (V) comprising first valve (120) and the second valve (140) are linear type directional and flow control valve such as but not limited to 3 way, 2-position spool valves, that are actuated by linear actuators using electric, pneumatic, hydraulic and mechanical powers. The linear movement of first and second valves (120 and 140) between first and second positions selectively allows flow of biological sample and one or more fluids into or out of the matrix chamber (130). In an embodiment of the present disclosure, the one or more fluids are elute materials (or simply elute) which contain nucleic acids and waste fluids. In another embodiment, the one or more fluids contain elute materials (or simply elutes) which contain nucleic acids, and rest of the one or more fluids are waste fluids.

Figure 5B:
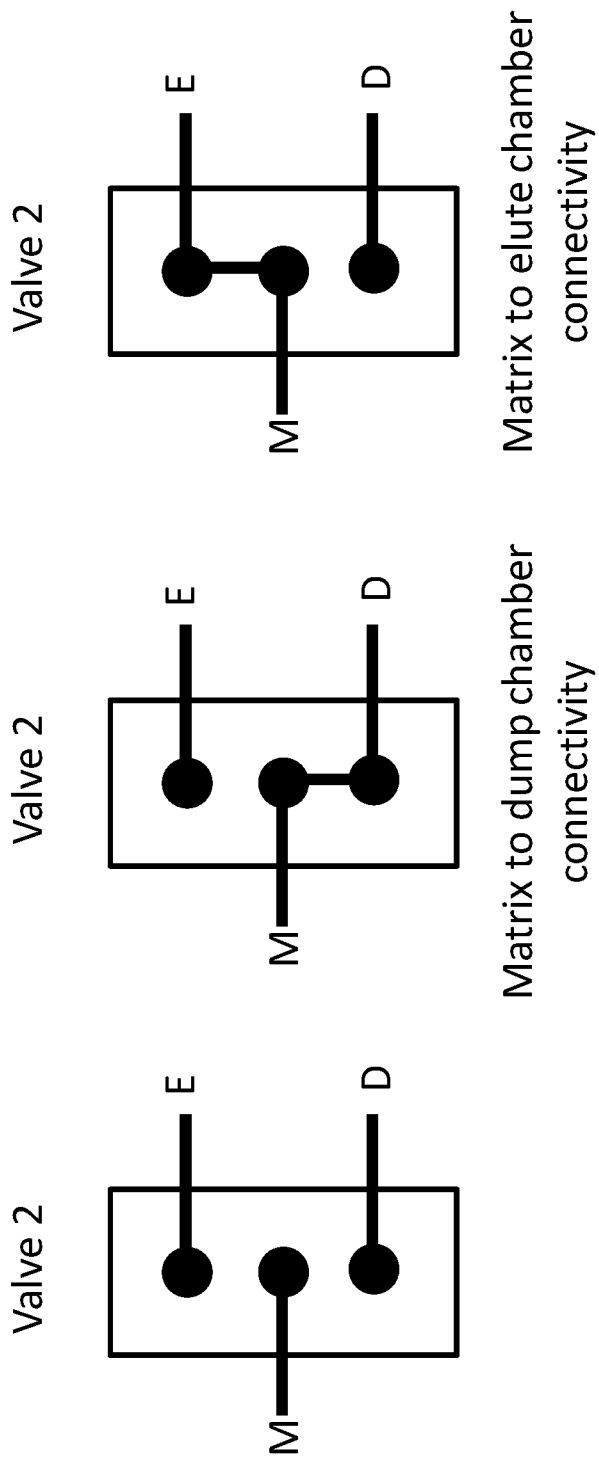
FIG. 5B illustrates schematic diagrams of the second valve actuated between different positions, according to an exemplary embodiment of the present disclosure.

The biological sample with or without buffer and the reagent solutions combine and get mixed in the matrix chamber (130). The flow of biological sample with or without buffer and the reagent solutions into the matrix chamber (130) through the first valve (120) is facilitated by differential pressure created by the pump (105) controlled by the control unit (112). The heating element (106) explained in previous paragraphs heats the mixture in the matrix chamber (130) to separate nucleic acids from waste materials. In an embodiment, the heat added to the matrix chamber is in the range of 60 degrees to 95 degrees for a period ranging from 5-25 minutes. The separated nucleic acids and waste fluids are routed into separate collection chambers via matrix outlet (140A) into one or more valves (V). In an embodiment, the one or more valves (V) that route separated nucleic acid and waste fluid is a second valve (140). The second valve (140) is configured to move to first position (as shown in FIG. 5B) to allow flow of nucleic acid fluids from matrix chamber (130) into the elute collection chamber (150) via channel (140B), and moves to second position (as shown in FIG. 5B) to allow flow of waste fluids from matrix chamber (130) to dump chamber (160) via channel (140C). The second valve (140) includes but not limited to two-position, three way directional control valve which allows flow of elute from the matrix chamber (130) in one instant, and waste fluids from the matrix chamber (130) in another instant. The fluid obtained at the elute chamber (150) is taken out and subjected to further processes like PCR, etc. The waste fluids in dump chamber (160) will be disposed off at the time of disposing off the cartridge (103). The flow of fluids from the matrix chamber (130) into elute chamber (150) and dump chamber (160) through the second valve (140) is facilitated by differential pressure created by the pump (105) controlled by the control unit (112). In an embodiment, the pump (105) is selected from group such as but not limited to syringe pump, peristaltic pumps or other positive displacement pumps which serves the purpose of driving the biological samples and the one or more fluids described above inside the cartridge (103). Further, the movement of first and second valves (120, 140) between first and second positions is facilitated by the one or more actuators (107) which reside outside the cartridge (103), and the actuators (107) are controlled by control unit (112).

The matrix chamber (130) [shown in FIG. 4] comprises a binding matrix which is configured to capture organisms and/or nucleic acids from the mixture of biological samples and the reagent solutions. In an exemplary embodiment, the binding matrix is configured with a mesh type structure for trapping the nucleic acids on its surface. In an embodiment, the binding matrix is selected from group such as but not limiting to natural cotton, surgical cotton, clinical grade cotton, commercial cotton, spun cotton, water washed cotton, acid or base washed cotton, autoclaved cotton, buffer treated cotton having pH ranging from about 1 to about 14, salt solution treated cotton, organic solvent treated cotton, pressed cotton and processed cotton. In an embodiment of the present disclosure, the matrix chamber comprises matrix selected from a group comprising cotton, derivatives of cotton and synthetic polymers having blends of cotton or any combination thereof. Furthermore, the quantity of binding matrix added to the matrix chamber, not limiting to cotton, is dependent on the volume of the biological sample; and for samples in the range of 1-500 µl (Eg: Blood 250 µl or sputum 500 µl), 5-30 mg, preferably 15 mg of cotton is adequate. For volumes of samples in the range of milliliters, a 50 mg or more of cotton is essential. Overall, 1 milligram to 10 grams of cotton is sufficient to extract nucleic acids from any clinical, environmental or field samples. In the suspension solution, the components that are to be filtered from the mixture of biological sample and reagent solutions have affinity towards the surface of the cotton matrix. Thus, the organisms and/or nucleic acids in the suspension solution are collected or trapped on the binding matrix. The remaining fluid in the suspension solution gets seeped through the binding matrix, due to lack of affinity. In an embodiment, the binding matrix is washed by passing the buffer solution, to remove impurities from biological sample collected on the surface of the binding matrix. Subsequent to purification the nucleic acids captured/bound from the biological samples and the reagent solutions are released by applying heat to the binding matrix. The released nucleic acids are collected into the elute collection chamber (150). The collected nucleic acids are later processed by PCR analysis and detection. The waste collection chamber (160) includes an absorbent material for absorbing the waste fluids received from the matrix chamber (130) via the channel (140C). In an embodiment, the absorbent material is selected from group such as but not limiting to sponge. Absorption of waste fluids will enable to prevent spillage of waste fluids to the surroundings during and after purification of biological samples. This makes the use of cartridge (103) eco-friendly, hygienic and bio-safe for usage and disposal.

FIGS. 7A and 7B are exemplary embodiments which illustrate exploded top view and exploded perspective view respectively of a docking mechanism (175) provided in the device (100). The docking mechanism (175) is intended to dock the cartridge (103) inside device (100) to interface the cartridge (103) elements with the components of the device (100). The docking mechanism is designed such that it allows the cartridge (103) to be loaded linearly (vertically or at an inclination) with respect to the device (100). The mechanism (180) comprises a fixed member (180) which can receive and hold the cartridge (103), and a movable member (181) which can impart reciprocating movement to the fixed member (180) via guide shafts (180D) for docking the cartridge (103) with the device (100), and un-docking the cartridge (103) from the device (100). In an embodiment, the fixed and movable members (180, 181) include but not limited to plates, blocks and the like having rectangular or square shapes. The fixed member (180) is held or secured to the movable member (181) by securing means, including but not limited to fasteners.

The other side of the movable member (181) is connected to an actuator (105B) which reciprocatingly actuates the movable member (181). The reciprocating movement of the movable member (181) imparts reciprocating motion to the fixed member (180) via guide shafts (180D) to pull the cartridge (103) towards the actuator (105B) for the purpose of docking, and push away the cartridge (103) for the purpose of un-docking. The actuator (105B) includes but not limited to a linear actuator such as piston cylinder arrangement. In an embodiment, the actuator (105B) is a rotary actuator such as but not limited to stepper motor which imparts rotary motion to drive one or more lead screws (180E), and rotation of lead screws (180E) causes linear movement of movable and fixed members (180, 181). The mechanism comprises a locking arrangement (180A), such as but not limited to a locking lever to lock the fixed member (180) with the device (100) in docked position, and a release arrangement (180B) such as a release lever to release the fixed member (180) from the device (100) for the purpose of un-docking.

Figure 6:
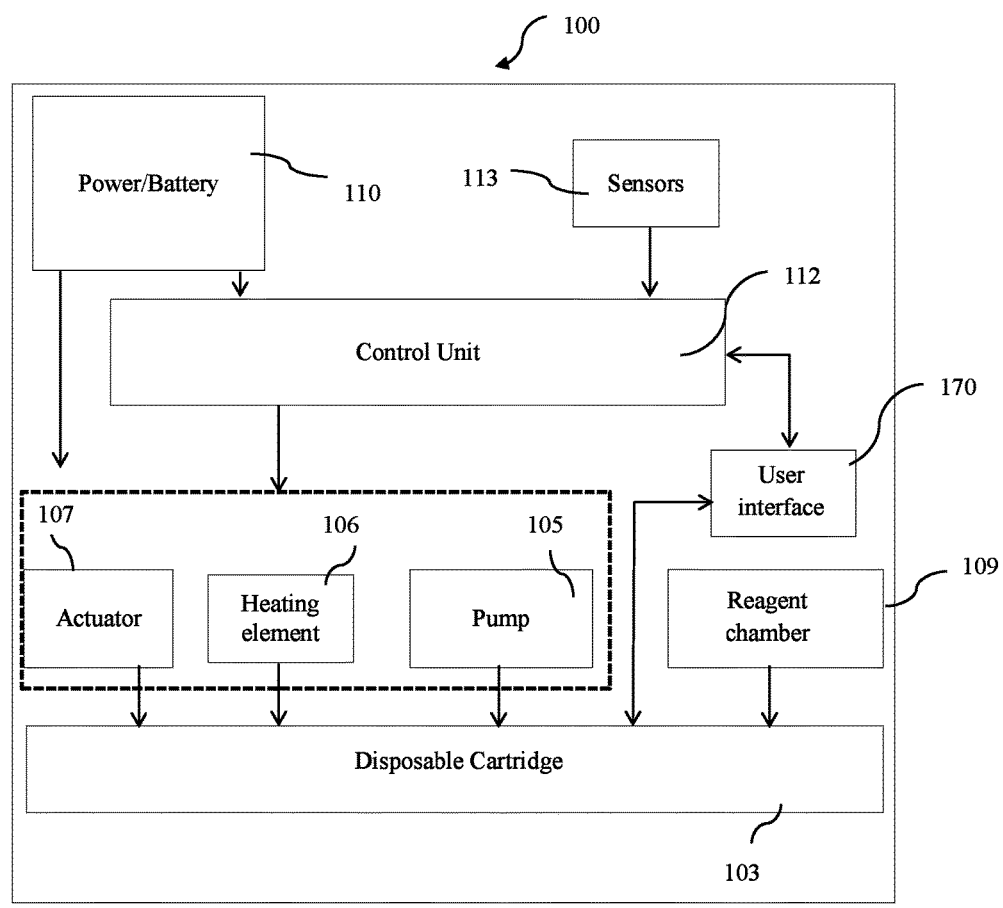
FIG. 6 illustrates schematic block diagram of the device for purifying biological sample, according to exemplary embodiment of the present disclosure.

In an embodiment of the present disclosure, there is provided a method for purifying biological samples. The method comprises steps of firstly, operating by a control unit (112), at least one actuator (107) to actuate one or more valves i.e. the first valve (120) and the second valve (140) configured in at least one cartridge (103). The actuation of the one or more valves (V) [here the first valve (120)] selectively allows flow of the biological sample and one or more reagent solutions into a matrix chamber (130) of the cartridge (103). In a second step, the method comprises activating, by the control unit (112), at least one heating element (106) for heating the matrix chamber (103). Heating of the matrix chamber (130) increases the temperature of mixture of biological sample and one or more reagent solutions. The increase in temperature isolates nucleic acids from impurities which are contained in the matrix chamber (130). This is followed by the third step which involves operating the at least one actuator (107) by the control unit (112) to actuate the one or more valves (here second valve (140)) to selectively allow flow of the nucleic acid and waste fluids from the matrix chamber (130) into the elute collection chamber (150) and dump chamber (160) respectively. The method also comprises act of operating one or more pumps (105) for facilitating flow of biological samples and one or more fluids in the cartridge (103). The pump (105) is configured to maintain differential pressure across the cartridge (103) to enable circulation of the biological sample, reagent solutions, elute and waste fluids. The plurality of sensors provided in the device (100) sense one or more process parameters including but not limited to at least one of temperature of the matrix chamber (130), pressure of the biological sample and the one or more fluids, positions of the one or more valves (V), and presence of the at least one cartridge (103) and send signals to the control unit (112) to provide appropriate outputs via the user interface. The battery (110) [shown in FIG. 6] provided in the device (100) supplies power to the pump (105), the actuators (107), the heating element (106) and other active and passive components of the device (100) for operation. The interface between each of the components in the device (100) is depicted in the block diagram shown in FIG. 6.

In an embodiment of the present disclosure, the one or more buffer solutions used for purifying biological samples as states above is selected from a group comprising lysis buffer, binding buffer, washing buffer and elution buffer or any combination thereof; more specifically as envisaged in the published US Application, numbered US 2013/203150. In an embodiment of the present disclosure, the lysis buffer is selected from a group comprising guanidine thiocyanate, guanidine hydrochloride, EDTA, Tris, detergent, polyol, monovalent salt containing group IA cation or divalent salt containing group IIA cation and protein digesting enzyme optionally along with urea or any combination thereof.

In an embodiment of the present disclosure, the EDTA is of concentration ranging from about 0.10 mM to about 300 mM, preferably about 50 mM. In an embodiment of the present disclosure, the guanidine thiocyanate or the guanidine hydrochloride is of concentration ranging from about 0.1 M to about 7 M, preferably about 3.5 M. In an embodiment of the present disclosure, the Tris is of concentration ranging from about 0.01 mM to about 300 mM, preferably about 200 mM. In an embodiment of the present disclosure, the polyol is of concentration ranging from about 0.01% to about 30% (v/v), preferably about 5% (v/v). In an embodiment of the present disclosure, the detergent is selected from a group comprising sodium lauryl sulphate, sodium dodecyl sulphate, Triton X-100, Tween 20 and NP-40 or any combination thereof and wherein the protein digesting enzyme is proteinase K.

In an embodiment of the present disclosure, the binding buffer is water optionally along with polyols or non-polyols. In an embodiment of the present disclosure, the polyol comprises water soluble polyol compounds selected from a group consisting of Poly-ethylene glycol, glycerol, Polypropylene glycol, ethylene glycol and propylene glycol. In an embodiment of the present disclosure, the non-polyol comprises alcohols consisting of methanol, ethanol, isopropanol or any water-soluble liquid with a functional group of acid, amine, alcohol, phenol, amide or ester as one of the functional groups; or any combination thereof. In an embodiment of the present disclosure, the washing buffer comprising a first wash with washing buffer comprising about 1% to about 99% (v/v), preferably about 30% to about 70% (v/v) and optimally about 75% (v/v) of aqueous alcohol followed by multiple washes with a washing buffer comprising aqueous buffer.

In an embodiment of the present disclosure, the aqueous alcohol is selected from a group comprising ethanol, methanol, n-propanol, 2-propanol, glycerol, PEG, PPG, ethylene glycol and propylene glycol.

In an embodiment of the present disclosure, the water is selected from a group comprising deionized water, DNase free water, RNase free water, MilliQ water, filtered water, tap water and ground water or any combination thereof.

In an embodiment of the present disclosure, the said washing buffer can optionally comprise salts selected from a group comprising MgCl2, CaCl2, NaCl and KCl, or buffers selected from a group comprising bicine, tricine, Tris, HEPES, CHAPS, phosphate, acetate, IVIES, pyridine, piperazine, Bis-tris, PIPES, ACES, BES, TES, borate, TAPS, CHES, CAPS, ethanolamine and piperidine, having pH ranging from about 5 to about 12.

In an embodiment of the present disclosure, the eluting buffer comprises warm water having temperature ranging from about 45° C. to about 99° C. along with buffer or salt, having pH ranging from about 8 to about 11. In an embodiment of the present disclosure, the water is selected from a group comprising deionized water, DNase free water, RNase free water, MilliQ water, filtered water, tap water and ground water or any combination thereof.

In an embodiment of the present disclosure, the buffer is selected from a group comprising bicine, tricine, Tris, HEPES, CHAPS, phosphate, acetate, IVIES, pyridine, piperazine, Bis-tris, PIPES, ACES, BES, TES, borate, TAPS, CHES, CAPS, ethanolamine and piperidine or any combination thereof having pH ranging from about 5 to about 12 or having pKa ranging from about 7 to about 10.

In an embodiment of the present disclosure, the salt is selected from a group comprising MgCl2, CaCl2, NaCl and KCl or any combination thereof in the concentration ranging from about 0.01 mM to about 100 mM, preferably in the range of about 5 mM to about 50 mM.

In an embodiment of the present disclosure, the purified nucleic acid eluted from the matrix present in the device is processed using real-time PCR. Said amplification of nucleic acid enables detection of infection/disease causing organism if present in the biological samples with heightened specificity and sensitivity. By way of exemplification, the device of the present disclosure is enabled for showcasing its working not only in purification of nucleic acids, but also its effective application in identification of deadly infection such as Malaria, Chikungunya, Typhoid and Tuberculosis in the biological samples, by employing real-time PCR amplification reaction.

The present disclosure embodies extraction of DNA of Typhoid causing bacteria belonging to Salmonella sp. in new cartridges by employing spiked blood as the biological sample. Synthetic DNA from Salmonella sp. bacteria was spiked in the blood sample

TABLE 1

| Extraction Details [BLOOD] | Target Ct (in triplicates) |
| --- | --- |
| Cartridge-1 | 30.31 |
|  | 30.32 |
|  | 30.41 |
| Cartridge-2 | 29.67 |
|  | 30.33 |
|  | 29.76 |
| Cartridge-3 | 30.72 |
|  | 30.39 |
|  | 31.52 |
| Qiagen control | 28.77 |
| (spin column protocol, commercial kit) | 28.8 |
|  | 28.72 |

Inference: As can be observed from Table 1, the Ct levels of Target, here Salmonella sp. by employing a commercial Qiagen control is lower when compared to Ct levels obtained by employing the device of the present disclosure, thus being effective in identification of Typhoid infection levels in a biological sample, not limiting to blood alone.

The present disclosure also embodies, Chikungunya virus extractions in new cartridges by employing spiked blood as the biological sample. Synthetic Chikungunya virus RNA was spiked in whole blood samples.

TABLE 2

| Extraction Details [BLOOD] | Target Ct (triplicates) |
| --- | --- |
| Cartridge-1 | 25.45 |
|  | 26.02 |
|  | 26.94 |
| Cartridge-2 | 26.94 |
|  | 27.87 |
|  | 27.28 |
| Cartridge-3 | 27.99 |
|  | 28.86 |
|  | 29.46 |
| Qiagen control | 21.34 |
| (spin column protocol, commercial kit) | 21.34 |
|  | 21.62 |

Inference: As can be observed from Table 2, the Ct levels of target, here Chikungunya virus, by employing a commercial Qiagen control is lower when compared to Ct levels obtained by employing the device of the present disclosure, thus being effective in identification of Chikungunya infection levels.

The present disclosure also embodies, extractions of Mycobacterium tuberculosis (MTB) DNA in new cartridges by employing spiked sputum as the biological sample. MTB DNA obtained from ATCC was spiked in sputum.

TABLE 3

| Exp. Details [Sputum] | Target Ct |
| --- | --- |
| Cartridge-1 | 30.99, 30.90 |
| Cartridge-2 | 30.03, 30.06 |
| Cartridge-3 | 29.01, 29.11 |
| Cartridge-4 | 29.72, 29.69 |

TABLE 3-continued

| Exp. Details [Sputum] | Target Ct |
|---|---|
| Cartridge-5 | 30.27, 30.18 |
| Control Qiagen | 30.17, 29.89 |

Inference:

As can be observed from Table 3, the Ct levels of target, here M. Tuberculosis, by employing a commercial Qiagen control is relatively lower when compared to Ct levels, by employing the device of the present disclosure, thus being effective in identification of M. Tuberculosis infection levels in biological samples, not limiting to sputum alone.

The present disclosure also embodies, second set of experiments showing use of the device in extracting synthetic Chikungunya RNA, synthetic *Salmonella* DNA and synthetic DNA of *Plasmodium vivax* in new cartridges employing blood as the biological sample.

TABLE 4

| Experimental Details - Blood | Target Ct (*Salmonella*) in duplicates | Target Ct (P. vivax) in duplicates | Target Ct (Chikungunya virus) in duplicates |
|---|---|---|---|
| Catridge-1 | 23.04, 23.35 | 18.87, 19.01 | 27.46, 27.58 |
| Catridge-2 | 23.25, 23.07 | 18.94, 18.72 | 27.4, 27.4 |
| Qiagen (control) | 23.45, 23.29 | 18.54, 18.5 | 26.5, 26.25 |

Inference:

As can be observed from Table 4, the Ct levels of targets, here Chikungunya, Typhoid and Malaria, by employing a commercial Qiagen control is mostly lower when compared to Ct levels, by employing the device of the present disclosure, thus being effective in identification of Chikungunya virus, *Salmonella* bacteria and malaria causing *Plasmodium vivax* infection levels.

It is to be understood that a person of ordinary skill in the art would develop a portable device of any configuration without deviating from the scope of the present disclosure. Further, various modifications and variations may be made without departing from the scope of the present invention. Therefore, it is intended that the present disclosure covers such modifications and variations provided they come within the ambit of the appended claims and their equivalents.

Advantages:

The present disclosure provides a biological sample purification device which uses miniaturized components and a compact power supply system that makes the device portable and compact.

The present disclosure provides a biological sample purification device that is uses a disposable cartridge in which the waste fluids are stored. The waste fluids are disposed off at the time of disposal of the cartridge, thereby rendering the waste disposal bio-safe.

The present disclosure provides a biological sample purification device which uses components that do not require continuous supply of AC power supply. This makes the device to be carried between places and use the device in remote locations where availability of power is little or nil.

EQUIVALENTS

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Referral numeral | Description |
| --- | --- |
| 100 | Portable device |
| 101 | Housing |
| 102 | Cartridge holder |
| 102A | Cartridge loading door |
| 102B | Cartridge holding recess |
| 102C | Slider latch assembly |
| 102D | Solenoid actuator for slider latch assembly |
| 103 | Cartridge |
| 103A | First chamber |
| 103B | Second chamber |
| 103C, 103D | Inlet, Outlet of first chamber |
| 103E, 103F | Inlet port, Outlet port of second chamber |
| 104 | Fluid handling manifold |
| 105 | Pump |
| 105A | Auxiliary pump |
| 105B | Actuator |
| 106 | Heating element |
| 107 | Actuator |
| 107A, 107B | First actuator, second actuator |
| V | One or more valves |
| AV | Auxiliary valves |
| 108A, 108B | Flow elements |
| 108C, 108D | Nozzles |
| 109 | Reagent holding unit |
| 110 | Battery |
| 111 | Damper |
| 112 | Control unit |
| 120, 140 | First valve, second valve |
| 130 | Matrix chamber |
| 140A | Outlet of matrix chamber |
| 140B | Inlet of elute collection chamber |
| 140C | Inlet of dump chamber |
| 150 | Elute collection chamber |
| 160 | Dump chamber |
| 165, 165A | Sample heating element, holder |
| 170 | User interface |
| 170A | Input interface |
| 170B | Output interface |
| 175 | Docking mechanism |
| 180 | Fixed plate |
| 181 | Movable plate |
| 180A | Locking arrangement |
| 180B | Release arrangement |
| 180D | Guide shaft |
| 180E | Guide pins |

We claim:

1. A portable device for purifying biological sample, the device comprising:
a housing;
a cartridge holder accommodated in the housing for holding at least one cartridge, the at least one cartridge is configured to purify the biological sample;
at least one pump positioned in the housing, the at least one pump is fluidly connectable to the at least one cartridge and is configured to circulate the biological sample and one or more fluids through the at least one cartridge;
at least one heating element configured in the housing to selectively heat a matrix chamber in the at least one cartridge;
at least one actuator disposed in the housing and outside the cartridge, wherein the at least one actuator comprises:
a first actuator coupled to a first valve of one or more valves; and
a second actuator coupled to a second valve of the one or more valves; and
a control unit communicatively interfaced with the at least one actuator, the at least one heating element and the at least one pump, wherein the control unit is configured to:
transmit, a first signal to the first actuator to operate the first valve in the at least one cartridge to selectively allow flow of the biological sample and one or more reagent solutions into the matrix chamber;
transmit, a second signal to the second actuator to operate, the second valve in the at least one cartridge to selectively allow flow of an eluted material from the matrix chamber to a collection chamber of the at least one cartridge, and a waste fluid from the matrix chamber to a dump chamber of the at least one cartridge; and
regulate operation of the at least one pump and the at least one heating element during purification of the biological sample.

2. The device as claimed in claim 1, wherein the one or more fluids are at least one of one or more buffer solutions, one or more reagent solutions, the eluted material and the waste fluid.

3. The device as claimed in claim 1, wherein the at least one cartridge comprises at least one first chamber to hold the biological sample, and at least one second chamber configured to receive and hold one or more reagent solutions.

4. The device as claimed in claim 1 further comprises at least one container for holding one or more buffer solutions, and at least one reagent holding unit disposed in the housing for holding one or more reagent solutions.

5. The device as claimed in claim 1, wherein the one or more valves are two position, three-way directional control valves and flow control valves.

6. The device as claimed in claim 1, wherein the at least one actuator actuates the one or more valves between a first position and a second position.

7. The device as claimed in claim 1, wherein the eluted material is nucleic acid.

8. The device as claimed in claim 1, wherein the at least one pump is configured to maintain a differential fluid pressure in the at least one cartridge to enable flow of the biological sample and the one or more fluids through the at least one cartridge.

9. The device as claimed in claim 1, wherein the control unit is configured to selectively operate a combination of the at least one pump and the at least one actuator, and the at least one heating element.

10. The device as claimed in claim 1, wherein the at least one pump, the at least one heating element and the at least one actuator are powered by a battery configured in the device.

11. The device as claimed in claim 1 comprises a plurality of sensors configured to detect a plurality of process parameters inside the device.

12. The device as claimed in claim 11, wherein the plurality of process parameters includes temperature of the matrix chamber, pressure of the biological sample and the one or more fluids, positions of the one or more valves, and presence of the at least one cartridge.

13. The device as claimed in claim 1 comprises a mechanism for docking the at least one cartridge.

* * * * *